US010449013B2

United States Patent
Jochinsen

(10) Patent No.: US 10,449,013 B2
(45) Date of Patent: Oct. 22, 2019

(54) ANTI-PARALLAX CORRECTION OF STEREOSCOPIC SURGICAL IMAGES

(71) Applicant: Novartis AG, Basel (CH)

(72) Inventor: Mauricio Jochinsen, Fountain Valley, CA (US)

(73) Assignee: Novartis AG (CH)

( * ) Notice: Subject to any disclaimer, the term of this patent is extended or adjusted under 35 U.S.C. 154(b) by 0 days.

(21) Appl. No.: 15/946,415

(22) Filed: Apr. 5, 2018

(65) Prior Publication Data

US 2018/0296301 A1 Oct. 18, 2018

Related U.S. Application Data

(60) Provisional application No. 62/485,515, filed on Apr. 14, 2017.

(51) Int. Cl.
| | |
|---|---|
| *G06K 9/00* | (2006.01) |
| *A61B 90/00* | (2016.01) |
| *A61B 90/20* | (2016.01) |
| *G06T 7/73* | (2017.01) |
| *H04N 13/128* | (2018.01) |
| *H04N 13/361* | (2018.01) |
| *A61B 3/00* | (2006.01) |
| *A61B 3/10* | (2006.01) |
| *A61B 3/13* | (2006.01) |
| *A61F 9/007* | (2006.01) |
| *G02B 21/00* | (2006.01) |
| *G02B 21/22* | (2006.01) |
| *G02B 21/36* | (2006.01) |

(52) U.S. Cl.
CPC ............ *A61B 90/37* (2016.02); *A61B 3/0058* (2013.01); *A61B 3/102* (2013.01); *A61B 3/13* (2013.01); *A61B 3/132* (2013.01); *A61B 90/20* (2016.02); *A61F 9/007* (2013.01); *G02B 21/0012* (2013.01); *G02B 21/22* (2013.01); *G02B 21/365* (2013.01); *G06K 9/00671* (2013.01); *G06T 7/73* (2017.01); *H04N 13/128* (2018.05); *H04N 13/361* (2018.05); *A61B 2090/3735* (2016.02); *G06T 2207/20228* (2013.01); *G06T 2207/30041* (2013.01)

(58) Field of Classification Search
None
See application file for complete search history.

(56) References Cited

U.S. PATENT DOCUMENTS

| 2016/0183779 A1* | 6/2016 | Ren | ...................... A61B 3/0058 351/206 |
| 2017/0035287 A1* | 2/2017 | Ren | ...................... G06T 7/0012 |

FOREIGN PATENT DOCUMENTS

JP 2014175965 A 9/2014

* cited by examiner

*Primary Examiner* — Robert J Craddock
(74) *Attorney, Agent, or Firm* — Keiko Ichiye, Esq.

(57) ABSTRACT

Methods and systems for anti-parallax correction of stereoscopic surgical images may employ a stereoscopic surgical microscope to generate overlay content as left and right digital images that are overlaid on respective left and right analog images from an objective field of view of the surgical microscope. The user may select a location-dependent feature in the overlay content and may select left or right for the anti-parallax correction.

17 Claims, 4 Drawing Sheets

ANTI-PARALLAX CORRECTION OF STEREOSCOPIC SURGICAL IMAGES

TECHNICAL FIELD

The present disclosure relates to surgery and surgical equipment, and more specifically, anti-parallax correction of stereoscopic surgical images.

DESCRIPTION OF THE RELATED ART

In ophthalmology, ophthalmic surgery is performed on the eye and accessory visual structures to save and improve the vision of tens of thousands of patients every year. However, given the sensitivity of vision to even small changes in the eye and the minute and delicate nature of many eye structures, ophthalmic surgery is difficult to perform and the reduction of even minor or uncommon surgical errors or modest improvements in accuracy of surgical techniques can make a tremendous difference in the patient's outcome.

Ophthalmic surgery is performed on the eye and accessory visual structures. During ophthalmic surgery, a patient is placed on a support, facing upward, under surgical imaging equipment, such as a surgical microscope, an optical coherence tomography (OCT) scanner, and a digital camera. The surgical imagining equipment produces images of the eye undergoing surgery.

In many types of surgery, including ophthalmic surgery, the surgical microscope includes stereoscopic optics for enabling a stereoscopic view of patient biostructures during surgery. However, a stereoscopic view under a surgical microscope may introduce parallax that may create an illusion of an apparent location of certain objects in the field of view, which is undesirable for the surgeon viewing the stereoscopic view.

SUMMARY

In one aspect, a method for displaying images during surgery is disclosed. The method may include displaying a left analog image in a left ocular of a surgical microscope and displaying a right analog image in a right ocular of the surgical microscope. In the method, the left analog image and the right analog image may be of an objective field of the surgical microscope. The method may also include generating a left digital image and a right digital image. In the method, the left digital image and the right digital image may include overlay content for display with the left analog image and the right analog image, respectively. The method may further include receiving a first indication of a location-dependent feature in the overlay content, and, responsive to the first indication, displaying the location-dependent feature in one of the left digital image and the right digital image.

In any of the disclosed embodiments of the method, the objective field may be used to view a patient subject to surgery using the surgical microscope, while the location-dependent feature may be associated with a biostructure of the patient. In the method, the biostructure may be a portion of an eye of the patient, while the surgery may be an ophthalmic surgery. In the method, the biostructure included in the location-dependent feature may be subject to an optical coherence tomography (OCT) scan performed using the surgical microscope.

In any of the disclosed embodiments, the method may further include receiving a second indication specifying one of the left digital image and the right digital image for removing the location-dependent feature.

In any of the disclosed embodiments of the method, displaying the location-dependent feature may further include performing digital processing on one of the left digital image and the right digital image. The digital processing may further include identifying a region corresponding to the location-dependent feature, and changing the content of the region identified.

Other disclosed aspects include a surgical microscope for displaying images during surgery, including an objective lens for viewing a patient during a surgery, a right ocular for viewing by a right eye of a user of the surgical microscope, a left ocular for viewing by a right eye of the user, and a controller enabled to generate a left digital image and a right digital image for display in the left ocular and the right ocular, respectively. The controller may be further enabled to perform operations corresponding to the method. A further disclosed aspect is the controller.

BRIEF DESCRIPTION OF THE DRAWINGS

For a more complete understanding of the present disclosure and its features and advantages, reference is now made to the following description, taken in conjunction with the accompanying drawings, which are not to scale, in which like numerals refer to like features, and in which.

DETAILED DESCRIPTION

Figure 1:
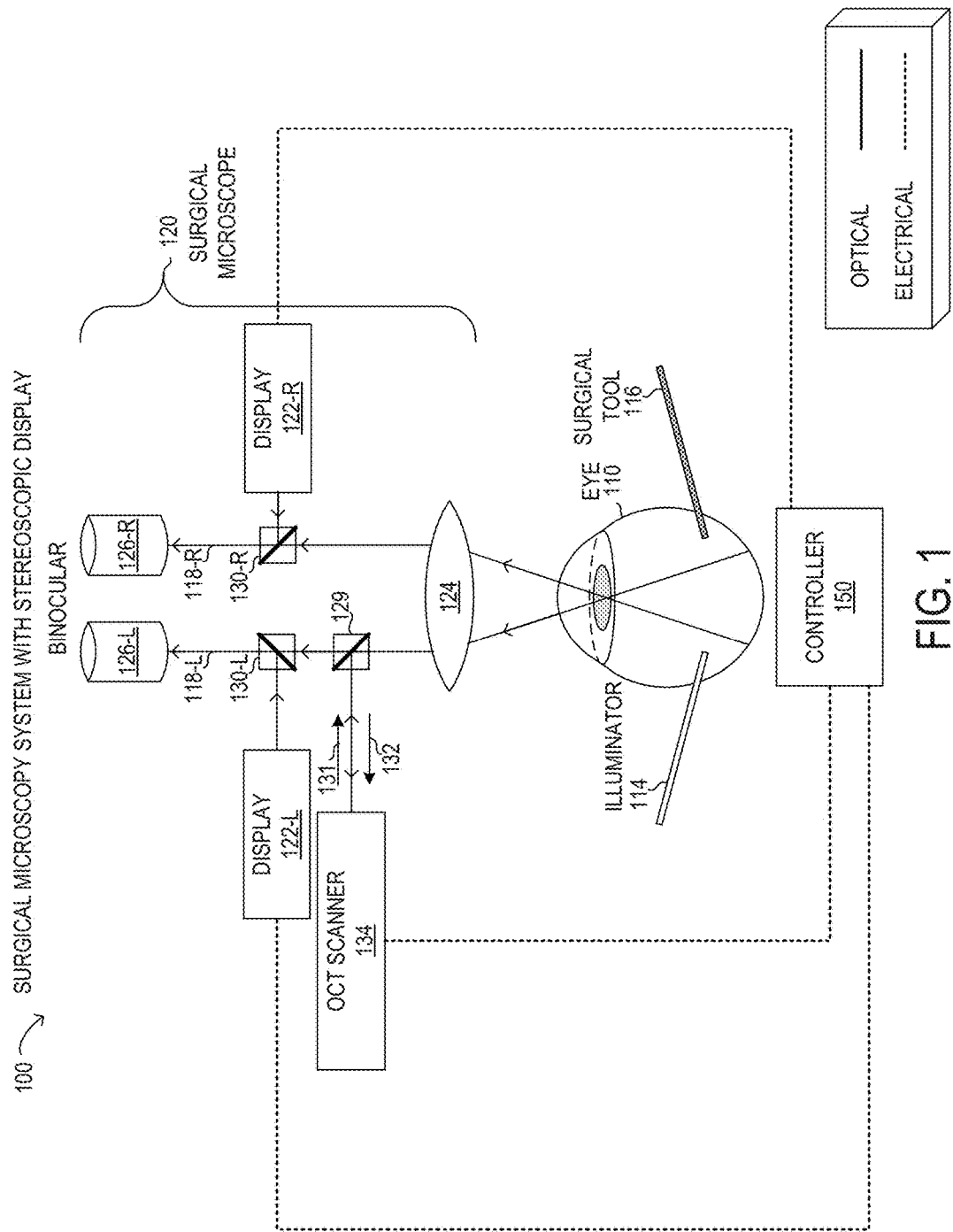
FIG. 1 is a schematic diagram of an ophthalmic surgical microscope system with a stereoscopic display.

In the following description, details are set forth by way of example to facilitate discussion of the disclosed subject matter. It should be apparent to a person of ordinary skill in the field, however, that the disclosed embodiments are exemplary and not exhaustive of all possible embodiments.

As used herein, a hyphenated form of a reference numeral refers to a specific instance of an element and the un-hyphenated form of the reference numeral refers to the collective element. Thus, for example, device '12-1' refers to an instance of a device class, which may be referred to collectively as devices '12' and any one of which may be referred to generically as a device '12'.

Augmented reality systems and virtual reality systems can project an individual image to each eye. These individual images, when perceived by both eyes, are interpreted by cognitive processes as a stereoscopic or three-dimensional (3D) image, just as the real world is normally perceived. In an augmented reality system, the stereoscopic image augments the normal view of the user and may be perceived as transparent or semi-transparent. In a virtual reality system, the stereoscopic image replaces all or a selected portion of the normal view of the user.

In both augmented reality systems and virtual reality systems, the stereoscopic image exhibits parallax, another feature of how the real world is perceived. Parallax is the apparent shift in location of an object or image caused by a change in the observation position. With respect to the eyes, parallax represents a displacement or difference in the apparent position of an object or image when seen by one eye, as opposed to the other eye, or using both eyes. Parallax with human eyes results from the fact that each eye is at a different location, typically a few inches apart.

The apparent shift in location caused by parallax may be useful in making some components of augmented reality and virtual reality images more realistic, for example by adding perspective, depth, or three-dimensionality. However, when a precise location of a component in an image is important, as may be the case during surgery using a surgical microscope, parallax of that component may be distracting, confusing, or disorienting for the viewer (i.e., the surgeon), with potential adverse effects on the ease of performing surgery or even surgical outcomes.

The present disclosure, therefore, provides systems and methods for avoiding parallax for certain objects that appear in overlay content of stereoscopic surgical images, while optionally retaining the stereoscopic nature of other objects displayed in the overlay content. For example, parallax may be avoided in augmented reality surgical images that are viewed using a surgical microscope, in which digitally generated overlay content is superimposed upon an analog image of an objective field captures by an objective lens of the surgical microscope. In various implementations described herein, the surgery may be an ophthalmic surgery.

In particular embodiments, the overlay content in stereoscopic ophthalmic surgical images may relate to OCT scans that are performed on an eye of a patient. For example, OCT scan images of a biostructure volume may be presented stereoscopically for improved visual cognition of the biostructure volume, which is desirable. At the same time, when the surgical microscope is also used to control a scan location of an OCT scan, a marker in the overlay content indicating the scan location may be removed from one of a left digital image and a right digital image. In this manner, parallax of the apparent marker location in a stereoscopic view may be avoided, because the parallax may interfere with a precise positioning of an OCT scan beam designated by the marker, relative to the biostructure.

The present disclosure provides systems and methods for use of overlay images that are superimposed with analog images provided by a surgical microscope. The surgical microscope displays analog images into a left and right ocular, respectively, that are generated from the objective field of the objective lens. Then, left and right digital images may be superimposed on the left and right analog images, respectively, to display the overlay content to the user of the surgical microscope. When the user indicates (e.g. by selection) a location-dependent feature in the overlay content, a controller associated with the surgical microscope may remove the location-dependent feature from one of the left digital image and the right digital image to avoid parallax when viewing the location-dependent feature. The location-dependent feature may be associated with a particular biostructure of the patient, such as a biostructure of the eye. The user may select activation of anti-parallax correction of stereoscopic surgical images, and may also select one of the left or right ocular for displaying the anti-parallax stereoscopic view.

FIG. 1 is a schematic diagram of a surgical microscopy system 100 with a stereoscopic display for performing surgery. FIG. 1 shows various optical and electrical connections and is not drawn to scale or perspective. Although surgical microscopy system 100 is described herein for purposes of ophthalmic surgery on an eye 110 of a patient, it will be understood that surgical microscopy system 100 may be used for other types of surgery in different implementations, such as to view various biostructures of the patient during surgery, as disclosed herein. As shown in FIG. 1, surgical microscopy system 100 includes a surgical microscope 120, a display 122, an OCT scanner 134, and a controller 150.

As shown, surgical microscope 120 is depicted in schematic form to illustrate optical functionality. It will be understood that surgical microscope 120 may include various other optical, electronic, mechanical components, in different embodiments. For example, various lenses and optical elements along ocular paths 118 have been omitted from FIG. 1 for descriptive clarity. Surgical microscope 120 includes at least one objective lens 124 through which light beams are reflected from a biostructure being examined in a field of view. As shown, the biostructure being examined in the field of view is eye 110, shown schematically with interior portions of eye 110 being viewed. It is noted that in some embodiments, a secondary lens, such as a contact or non-contact lens (not shown) may be used to view interior portions of the eye. At the same time, a surgical tool 116 and an illuminator 114 are shown penetrating the sclera of eye 110, which is a typical arrangement for various kinds of vitreoretinal surgery, for example. Although the arrangement shown in FIG. 1 is illustrative of vitreoretinal surgery, it will be understood that surgical microscope 120 may be used for different kinds of ophthalmic surgery, such as corneal surgery, cataracts, or other ophthalmic surgery, in different implementations.

As shown in FIG. 1, objective lens 124 may represent a selectable objective to provide a desired magnification or field of view of eye 110. Objective lens 124 may receive light from eye 110 that may be generated by surgical microscope 120, or another source, such as illuminator 114, in various embodiments. As shown in FIG. 1, a left ocular beam 118-L and a right ocular beam 118-R may be formed from light emerging from eye 110, such as light reflected back from a light source (not shown) that transmits incident light through objective lens 124, among other light sources.

In FIG. 1, surgical microscope 120 is shown with a binocular arrangement with two distinct but substantially equal light paths, namely left ocular beam 118-L and right ocular beam 118-R, that enable viewing with binoculars 126 that comprise a left ocular 126-L and a right ocular 126-R. From objective lens 124, left ocular beam 118-L may arrive at a partial mirror 129. Partial mirror 129 may be used to transmit a sample beam 131 to eye 110 from OCT scanner 134, and to receive a measurement beam 132 reflected back from eye 110 to OCT scanner 134. OCT scanner 134 may further be controlled in conjunction with controller 150, such as to direct sample beam 131 to desired portions of eye 110 during surgery using surgical microscope 120. Then, results of an OCT scan may be received by controller 150 and may be added as overlay content to left and right digital images that are output by displays 122. The OCT scan or OCT scan data may be visualized as overlay content that is displayed concurrently with the image of the field of view of objective lens 124 (i.e., the objective field). For example, an OCT scan beam, which may be invisible to the naked eye, may be represented as a marker that is then superimposed on exact locations of eye 110 being subject to an OCT scan. From partial mirror 129, left ocular beam 118-L may then pass to partial mirror 130-L, which is used to superimpose the left digital image from display 122-L on the analog image of the objective field. From partial mirror 130-L, left ocular beam 118-L may be transmitted to left ocular 126-L. It is noted that the placement of OCT scanner 134 and partial mirror 129 on left ocular beam 118-L is arbitrary and may occur on right ocular beam 118-R in some embodiments.

From objective lens 124, right ocular beam 118-R may arrive at a partial mirror 130-R, which is used to superimpose the right digital image from display 122-R on the analog image of the objective field. From partial mirror 130-R, right ocular beam 118-R may be transmitted to right ocular 126-R.

Display 122 may represent a digital display device, such as a liquid crystal display (LCD) array, a digital light processing (DLP) engine, or a liquid crystal on silicon (LCoS) projector, among others. Display 122-L may generate a digital image for left ocular 126-L, while display 122-R may generate a digital image for right ocular 126-R. In some embodiments, display 122 includes miniature display devices that output images to binoculars 126 for viewing by the user and are integrated within the ocular optics of surgical microscope 120. It is noted that display 122 may be a singular device with separate left and right display regions and is shown as 122-L and 122-R for descriptive clarity in FIG. 1.

In FIG. 1, controller 150 may have an electrical interface with display 122, for example, sending data indicative of an image. In this manner, controller 150 may generate overlay content for the digital image, may modify the overlay content as described herein, and may output the digital image with the overlay content to display 122 that is viewed at binoculars 126. Controller 150 may perform image processing on the digital data in real-time with relatively high frame refresh rates, such that a user of surgical microscope 120 may experience substantially instantaneous display with little or no latency. Display 122 may comply with a display standard for the corresponding type of display, such as video graphics array (VGA), extended graphics array (XGA), digital visual interface (DVI), high-definition multimedia interface (HDMI), etc. In particular implementations, controller 150 may perform anti-parallax correction in stereoscopic images, as disclosed herein.

In FIG. 1, surgical microscopy system is also shown including OCT scanner 134, which may operate to perform OCT scans of biostructures of the patient, such as biostructures in eye 110 (or other biostructures of the patient in other embodiments). As shown, a partial mirror 129 may be used to transmit a sample beam 131 to eye 110 from OCT scanner 134, and to receive a measurement beam 132 reflected back from eye 110 to OCT scanner 134. OCT scanner 134 may further be controlled in conjunction with controller 150, such as to direct sample beam 131 to desired portions of eye 110 during surgery using surgical microscope 120. Then, results of an OCT scan may be received by controller 150 and may be added to a display image that is output by display 122. In some embodiments, the OCT scan or OCT scan data may be visualized as overlay content that is displayed concurrently with the image of the field of view of objective lens 124. For example, an OCT scan beam, which may be invisible to the naked eye, may be represented as a marker in the overlay content at exact locations of eye 110 being subject to an OCT scan.

In operation of surgical system 100, a stereoscopic view in surgical microscope 120 using binoculars 126 may be displayed using left and right analog images from objective lens 124. Accordingly, a left analog image is displayed into ocular 126-L and a right analog image is displayed into ocular 126-R. When display 122 is used to superimpose the overlay content, the left digital image may be superimposed on the left analog image, while the right digital image may be superimposed on the right analog image.

When anti-parallax correction is desired for certain location-dependent features in the overlay content, controller 150 may be enabled to receive user input to identify the location-dependent feature. For example, controller 150 may receive user input identifying a certain region in the overlay content. Controller 150 may also be enabled to receive user input identifying specific objects displayed in the overlay content, such as by enabling the user to directly select the specific objects that are location-dependent with respect to the user's field of view and to the location of biostructures of the patient being viewed. Then, based on a user's preference for right ocular 126-R or left ocular 126-L, controller 150 may remove the specific object from one of the right digital image and the left digital image. In particular embodiments, removal of the specific object may be performed by not generating the specific object when the respective digital image is generated. In this manner, the specific object that is location-dependent is displayed with anti-parallax correction, while the remaining portions of the overlay content may be viewed stereoscopically (see also FIG. 2).

In other embodiments, various types of user input are contemplated for identifying the location-dependent feature. The user may use gestures, eye movements, or user input devices in different embodiments, to activate the anti-parallax display, and select the specific content for anti-parallax display. Additionally, the user may select one of the left and right digital image for anti-parallax stereoscopic correction. For example, the user may select left or right based on a dominant eye of the user.

Figure 2A:
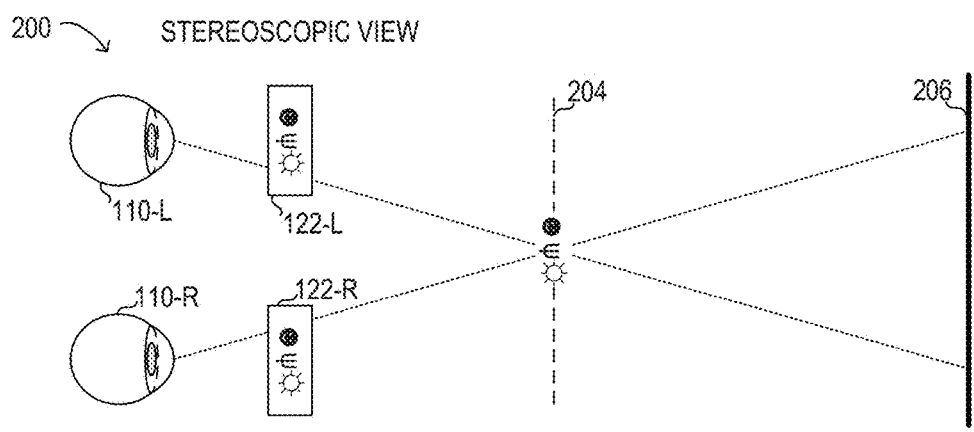
FIG. 2A is a schematic diagram of a stereoscopic view.

FIG. 2A illustrates a stereoscopic view 200 in an optical schematic diagram. Stereoscopic view 200 shows how left eye 110-L and right eye 110-R will result in a perceived image using stereoscopic operation of displays 122-L and 122-R. Specifically, when overlay content (shown using three graphical characters ●ψ☆) is displayed in both of displays 122-L and 122-R and viewed by eyes 110-L and 110-R, the image of all three characters will be perceived to appear by the viewer at a stereo plane 204 that is different from an image plane 206. The difference in perceived location of the image content is the result of stereoscopic image processing by the human visual cortex. However, the perceived location of stereo plane 204 is not coincident with image plane 206 and may create parallax when physical manipulations are performed at image plane 206, which is undesirable. It is noted that in surgical microscope 120 used for vitreoretinal surgery, for example, image plane 206 may correspond to the retina and may be curved.

Figure 2B:
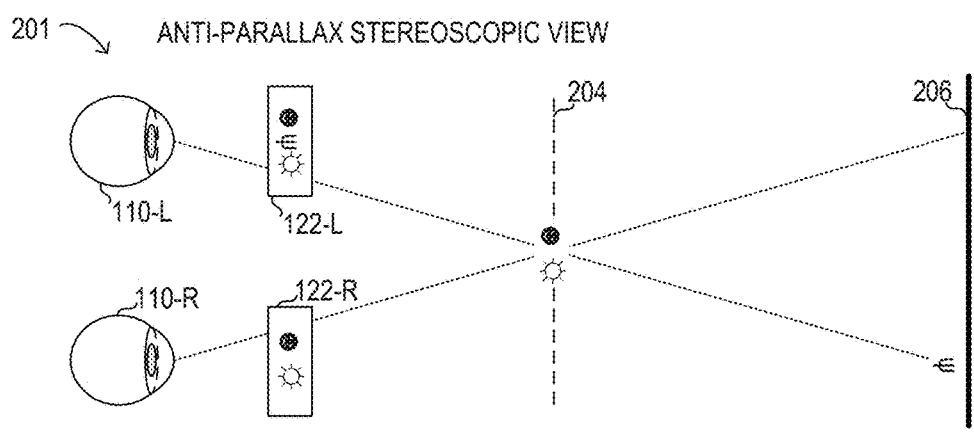
FIG. 2B is a schematic diagram of an anti-parallax stereoscopic view.

FIG. 2B illustrates an anti-parallax stereoscopic view 201 using the same arrangement as shown in FIG. 2A. In anti-parallax stereoscopic view 201, certain overlay content is displayed by display 122-L but not by display 122-R, while other overlay content is displayed by both displays to both eyes. Specifically, the character ψ is displayed in display 122-L only, while the characters ● ☆ are displayed in both displays 122-L and 122-R. As a result, the viewer will perceive the character ψ at image plane 206, corresponding to the physical location, rather than at the perceived location of stereo plane 204. At the same time, the viewer will perceive the characters the characters ● ☆ at the stereo plane 204. Thus, anti-parallax stereoscopic view 201 illustrates how parallax may be avoided for selected overlay content, while preserving the stereoscopic view for other overlay content in the same image frame. In particular embodiments, the overlay content displayed in one display only (e.g., the character ψ in display 122-L) may be oriented or shifted to correct for curvature of image plane 206, for example, when image plane 206 represents the retina.

Figure 3:
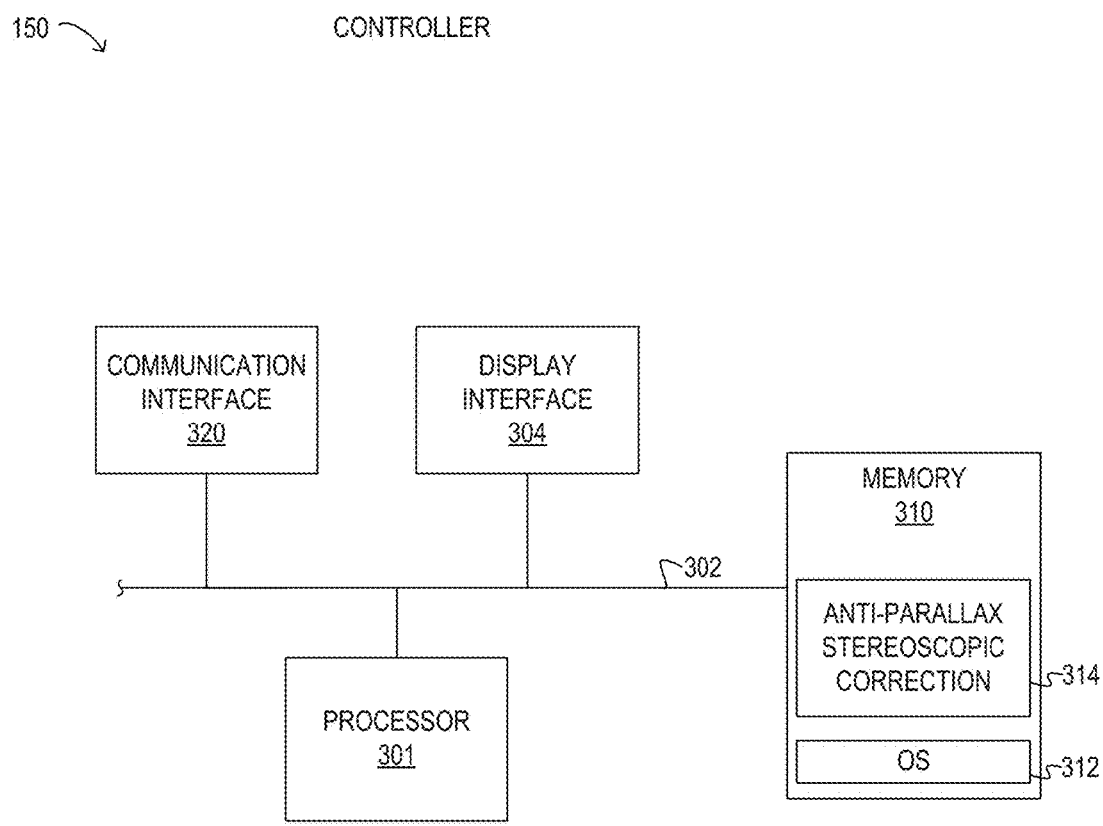
FIG. 3 is a schematic diagram of a controller.

Referring now to FIG. 3, a block diagram illustrating selected elements of an embodiment of controller 150, described above with respect to FIG. 1, is presented. In the embodiment depicted in FIG. 3, controller 150 includes processor 301 coupled via shared bus 302 to memory media collectively identified as memory 310.

Controller 150, as depicted in FIG. 3, further includes communication interface 320 that can interface controller 150 to various external entities, such as display 122, among others. In some embodiments, communication interface 320 is operable to enable controller 150 to connect to a network (not shown in FIG. 3). In embodiments suitable for anti-parallax correction of stereoscopic surgical images, controller 150, as depicted in FIG. 3, may include display interface 304 that connects shared bus 302, or another bus, with an output port for one or more displays, such as display 122 or an external display (not shown).

In FIG. 3, memory 310 encompasses persistent and volatile media, fixed and removable media, and magnetic and semiconductor media. Memory 310 is operable to store instructions, data, or both. Memory 310 as shown includes sets or sequences of instructions, namely, an operating system 312, and anti-parallax stereoscopic correction 314. Operating system 312 may be a UNIX or UNIX-like operating system, a Windows® family operating system, or another suitable operating system. Anti-parallax stereoscopic correction 314 may perform anti-parallax correction of stereoscopic surgical images, as described herein.

Figure 4:
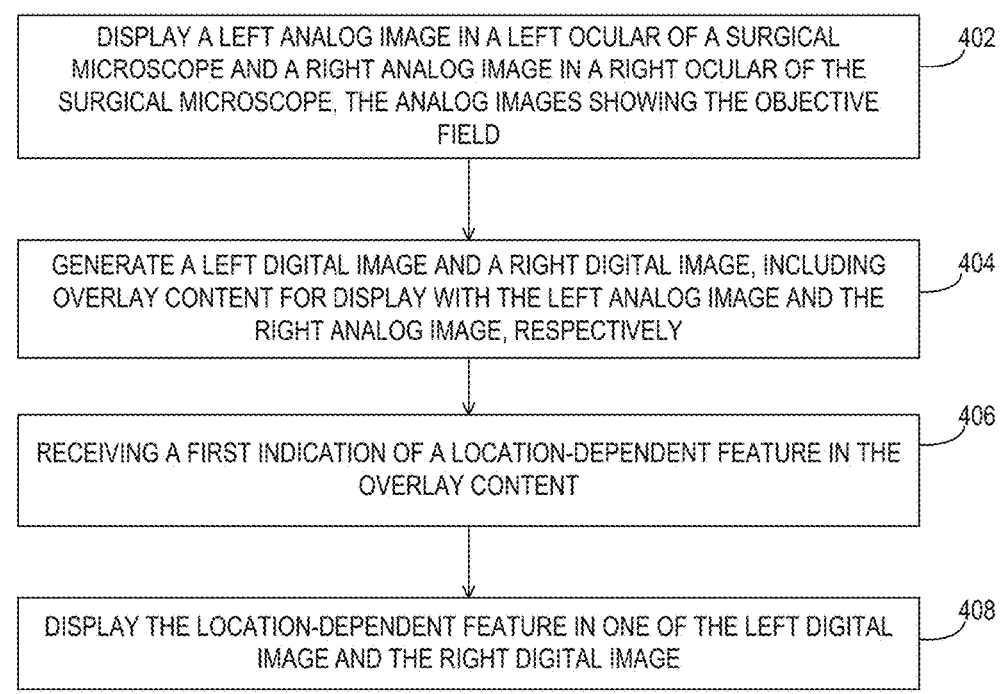
FIG. 4 is a flow chart of a method for anti-parallax correction in a stereoscopic surgical microscope.

FIG. 4 illustrates a method 400 for anti-parallax correction of stereoscopic surgical images, as described herein. Method 400 may be used in conjunction with the systems and apparatus described above. Method 400 may be used to perform anti-parallax correction of stereoscopic surgical images using surgical system 100 (see FIG. 1), for example, by executing anti-parallax stereoscopic correction 314 (see FIG. 3). Certain operations described in method 400 may be optional or may be rearranged in various surgeries using the systems and apparatuses of this disclosure.

At step 402, a left analog image is displayed in a left ocular of a surgical microscope and a right analog image is displayed in a right ocular of the surgical microscope, the analog images showing the objective field. In step 404, a left digital image and a right digital image are generated, including overlay content for display with the left analog image and the right analog image, respectively. At step 406, a first indication of a location-dependent feature in the overlay content is received. At step 408, the location-dependent feature is displayed in one of the left digital image and the right digital image.

As disclosed herein, methods and systems for anti-parallax correction of stereoscopic surgical images may employ a stereoscopic surgical microscope to generate overlay content as left and right digital images that are overlaid on respective left and right analog images from an objective field of view of the surgical microscope. The user may select a location-dependent feature in the overlay content and may select left or right for the anti-parallax correction.

The above disclosed subject matter is to be considered illustrative, and not restrictive, and the appended claims are intended to cover all such modifications, enhancements, and other embodiments which fall within the true spirit and scope of the present disclosure. For instance, any above system may include any above non-transitory computer readable medium and may carry out any above method. Any above non-transitory computer readable medium may also carry out any above method. Thus, to the maximum extent allowed by law, the scope of the present disclosure is to be determined by the broadest permissible interpretation of the following claims and their equivalents, and shall not be restricted or limited by the foregoing detailed description.

The invention claimed is:

1. A method for displaying images during surgery, the method comprising:
    displaying a left analog image in a left ocular of a surgical microscope, wherein the left analog image is of an objective field of the surgical microscope;
    displaying a right analog image in a right ocular of the surgical microscope, wherein the right analog image is of the objective field;
    generating a left digital image and a right digital image, wherein the left digital image and the right digital image include overlay content for display with the left analog image and the right analog image, respectively;
    receiving a first indication of a location-dependent feature in the overlay content, the location-dependent feature exhibiting a parallax where the feature is displaced in the left analog image relative to the right analog image; and
    responsive to the first indication, displaying the location-dependent feature in only one of the left digital image and the right digital image and not in the other of the left digital image and the right digital image to avoid the parallax.

2. The method of claim 1, wherein the objective field is used to view a patient subject to surgery using the surgical microscope, and wherein the location-dependent feature is associated with a biostructure of the patient.

3. The method of claim 2, wherein the biostructure is a portion of an eye of the patient, and wherein the surgery is an ophthalmic surgery.

4. The method of claim 3, wherein the biostructure associated with the location-dependent feature is subject to an optical coherence tomography (OCT) scan performed using the surgical microscope.

5. The method of claim 1, further comprising:
    receiving a second indication specifying one of the left digital image and the right digital image for removing the location-dependent feature.

6. The method of claim 1, wherein displaying the location-dependent feature further comprises:
    performing digital processing on one of the left digital image and the right digital image, the digital processing further comprising:
        identifying a region corresponding to the location-dependent feature; and
        changing the content of the region identified.

7. A surgical microscope for displaying images during surgery, the surgical microscope comprising:
    an objective lens for viewing a patient during a surgery, wherein an objective field of the objective lens is displayed as a left analog image in a left ocular of a surgical microscope, and as a right analog image in a right ocular of the surgical microscope;
    the right ocular for viewing by a right eye of a user of the surgical microscope;
    the left ocular for viewing by a left eye of the user;
    a controller enabled to:
        generate a left digital image and a right digital image, wherein the left digital image and the right digital image include overlay content for display with the left analog image and the right analog image, respectively;
        receive a first indication of a location-dependent feature in the overlay content, the location-dependent feature exhibiting a parallax where the feature is displaced in the left analog image relative to the right analog image; and responsive to the first indication, remove the location-dependent feature in only one of the left digital image and the right digital image and not in the other of the left digital image and the right digital image to avoid the parallax.

8. The surgical microscope of claim 7, wherein the objective field is used to view a patient subject to surgery using the surgical microscope, and wherein the location-dependent feature is associated with a biostructure of the patient.

9. The surgical microscope of claim 8, wherein the biostructure is a portion of an eye of the patient, and wherein the surgery is an ophthalmic surgery.

10. The surgical microscope of claim 9, wherein the biostructure included in the location-dependent feature is subject to an optical coherence tomography (OCT) scan performed using the surgical microscope.

11. The surgical microscope of claim 7, wherein the controller is further enabled to:

receive a second indication specifying one of the left digital image and the right digital image for removing the location-dependent feature.

12. The surgical microscope of claim 8, wherein the controller enabled to remove the location-dependent feature further comprises the controller enabled to:

perform digital processing on one of the left digital image and the right digital image, the digital processing further comprising:

identifying a region corresponding to the location-dependent feature; and changing the content of the region identified.

13. A controller for displaying images during surgery, the controller enabled to:

generate a left digital image and a right digital image, wherein the left digital image and the right digital image include overlay content for display with a left analog image and a right analog image, respectively displayed in a left ocular and a right ocular of a surgical microscope;

receive a first indication of a location-dependent feature in the overlay content, the location-dependent feature exhibiting a parallax where the feature is displaced in the left analog image relative to the right analog image; and responsive to the first indication, remove the location-dependent feature in only one of the left digital image and the right digital image and not in the other of the left digital image and the right digital image to avoid the parallax.

14. The controller of claim 13, wherein an objective field of an objective lens of the surgical microscope is used to view a patient subject to surgery, and wherein the location-dependent feature is associated with a biostructure of the patient.

15. The controller of claim 14, wherein the biostructure is a portion of an eye of the patient, and wherein the surgery is an ophthalmic surgery.

16. The controller of claim 13, wherein the controller is further enabled to:

receive a second indication specifying one of the left digital image and the right digital image for removing the location-dependent feature.

17. The controller of claim 13, wherein the controller enabled to remove the location-dependent feature further comprises the controller enabled to:

perform digital processing on one of the left digital image and the right digital image, the digital processing further comprising:

identifying a region corresponding to the location-dependent feature; and changing the content of the region identified.

* * * * *